United States Patent [19]

Laidler et al.

[11] 4,087,516

[45] May 2, 1978

[54] BODY SCANNING AGENT

[75] Inventors: John Barry Laidler; Maurice Alexander Alfred Stewart, both of Amersham, England

[73] Assignee: The Radiochemical Centre Limited, England

[21] Appl. No.: 775,643

[22] Filed: Mar. 7, 1977

[30] Foreign Application Priority Data

Mar. 19, 1976 United Kingdom ............... 11295/76

[51] Int. Cl.² ...................... A61K 29/00; A61K 43/00
[52] U.S. Cl. .......................................... 424/1; 23/259; 250/303; 252/313 R; 424/9; 424/1.5
[58] Field of Search ................ 252/313 R; 429/1, 1.5, 429/9; 23/259 R; 250/303

[56] References Cited

U.S. PATENT DOCUMENTS

| | | | |
|---|---|---|---|
| 3,723,612 | 3/1973 | Mikheev et al. ........................ 424/1 |
| 3,872,226 | 3/1975 | Haney et al. ............................ 424/1 |
| 3,875,299 | 4/1975 | Winchell et al. ....................... 424/1 |
| 3,968,221 | 7/1976 | Winchell et al. ....................... 424/1 |

*Primary Examiner*—Benjamin R. Padgett
*Assistant Examiner*—Christine M. Nucker
*Attorney, Agent, or Firm*—Wenderoth, Lind & Ponack

[57] ABSTRACT

A Technetium-99m labelled tin colloid for liver scanning is made by adding Technetium-99m, as an aqueous solution of pertechnetate ion $TcO_4^-$, to a reagent comprising one part by weight of sodium, potassium or ammonium fluoride and from 0.00075 to 0.75 parts by weight of stannous tin.

11 Claims, No Drawings

BODY SCANNING AGENT

Most current Technetium-99m liver scanning kits are based upon the formation of a Technetium-99m labelled sulphur colloid. This requires a three-component kit comprising sodium thiosulphate plus a colloid stabiliser as the first component, an acid as the second component and a neutralising buffer as the third component. The labelling procedure necessitates adding Tc-99m pertechnetate to the first component, followed by the acid component, heating the resultant mixture to precipitate lebelled colloidal sulphur, cooling to room temperature and finally buffering to a pH suitable for injection. The entire procedure takes about 15 to 20 minutes and must be carried out aseptically. Although the kit is widely used, there is an obvious need for a kit that can be used to prepare an injectable solution for liver scanning by a simple, one-step procedure performed at room temperature. One attempt to satisfy this need includes a kit based on Technetium-99m labelled phytate complex, which reacts with blood calcium after intravenous injection to form labelled, colloidal calcium phytate "in vivo". This kit satisfies the requirements outlined above, but needs to be used with caution because it interferes with blood calcium levels.

British Patent Specification No. 1,404,252 describes a kit comprising a colloidal solution of stannous chloride from which an injectable solution for liver scanning can be obtained simply by adding the eluate from a Technetium-99m generator. Control over colloid particle size of the stannous chloride solution is alleged to be achieved by rigorous exclusion of oxidising species. But colloidal solutions are inherently unstable, the particles being liable to aggregate or to adhere to the container wall. Accordingly, the shelf life of these kits is poor.

We believe that labelled stannous colloids will provide good liver scanning agents, and have sought to avoid the problems associated with the short shelf-lives of preformed colloids. Our approach to this problem, and the basis of our invention, is to provide a stabilised readily hydrolysable stannous tin complex which can be converted to colloidal form at the time of labelling with Technetium-99m.

Thus, the present invention provides a method of making a Technetium-99m labelled tin colloid, which method comprises adding Technetium-99m as an aqueous solution of pertechnetate ion $TcO_4^-$, to a reagent comprising one part by weight of sodium, potassium or ammonium fluoride and from 0.00075 to 0.75 parts by weight of stannous tin. The reagent may be in aqueous solution, but is preferably used as a freeze-dried solid. Suitably the solution of pertechnetate may be in water or in saline such as may conveniently be obtained by elution of a Technetium-99m generator; when the eluate is sterile, it is desirable that the reagent to which it is added should also be in a sterile state. There will normally be a large stoichiometric excess of stannous and fluoride ions over pertechnetate. The absolute amount of reagent used is governed by two parameters at different ends of the scale of use, i.e. at the lower end of the scale there must be sufficient reagent to reduce the Technetium-99m, whilst at the upper end of the scale toxicity of fluoride could become a limiting factor. Conveniently, from 2 to 50 mCi of Technetium-99m may be added to an amount of the above reagent containing 1 mg. of sodium, potassium or ammonium fluoride.

In another aspect, the present invention provides a packaged reagent for making Technetium-99m labelled tin colloids comprising:
Stannous tin, from 0.75 to 750 micrograms sodium, potassium or ammonium ion, from 50 to 7,000 micrograms,
fluoride, from 40 to 5,000 micrograms
and a container aseptically enclosing said reagent.

The reagent may be in aqueous solution, but is conveniently in freeze-dried form. The reagent may be prepared by providing in the container an aliquot of aqueous solution containing from 1 to 1,000 micrograms of stannous fluoride and from 0.1 to 10 milligrams of sodium, potassium or ammonium fluoride; freeze-drying the solution; sealing the container, preferably under a nitrogen atmosphere; and finally sterilising the sealed container and its contents e.g. by exposure to gamma irradiation. Alternatively, but less preferably, the whole preparation may be performed aseptically, thus rendering the terminal sterilisation step unnecessary. It is usual practice to provide an inert physiologically acceptable filler to provide bulk during the freeze-drying process; this invention contemplates the use of such a filler.

While we do not wish to be limited to any particular theory, we believe that what happens when the aqueous solutions of stannous fluoride and e.g. sodium fluoride are mixed, is that there is formed a weak, readily hydrolysable fluoro-stannite complex, which can be freeze-dried to avoid container incompatibility. We believe that the solution prepared by dissolving sodium fluoride in water and then adding stannous fluoride contains this fluoro-stannite anion $SnF_3^-$, and that the lyophilisate may be a mixture of sodium fluoro-stannite stabilised by excess sodium fluoride. We believe this product will have a shelf-life of at least six months. The complex may be converted to colloidal form simply by diluting it with water or isotonic saline containing pertechnetate ion. The dilution causes hydrolysis of the weak complex and simultaneous reduction and coprecipitation of the technetium with the colloidal tin hydrate.

Although we believe the lyophilisate to consist of a mixture of the fluoro-stannite complex and excess sodium fluoride, it is easier to describe our formulation in terms of the sodium fluoride and stannous fluoride originally dissolved in the aqueous stock solution. Our preferred formulation is:
125 micrograms of stannous fluoride
1 milligram of sodium fluoride.

We have tested variations down to 62.5 micrograms of stannous fluoride and up to 500 micrograms of stannous fluoride, keeping a fixed 1 milligram of sodium fluoride, with satisfactory results. We also know that samples in which the stannous fluoride has been partially oxidised, such that little as 10 to 12 micrograms of stannous ion remain, also behave satisfactorily. The stoichiometric quantity of sodium fluoride to form 1:1 complex with 125 micrograms of stannous fluoride is 43 micrograms, but we prefer to have an excess, to stabilise the complex during the preparation and dispensing stages and also to provide bulk during freeze-drying. If sodium fluoride is replaced by potassium fluoride or ammonium fluoride, possible toxicity differences may need to be taken into account.

The invention also contemplates the use of the Technetium-99m labelled tin colloidal solution for liver scanning. The solution is simply made by using a sterile aqueous saline solution of pertechnetate from a Technetium-99m generator to activate an aseptically packaged reagent as described above and shaking the container to ensure complete solution of the reagents. The resulting colloidal solution is ready for injection into the patient without further treatment.

The following Examples illustrate the invention.

EXAMPLE 1

(a) Preparation of reagent 1 gm of sodium fluoride is dissolved in 1 lt of nitrogen purged sterile water for injections. 125 mgm of stannous fluoride is then dissolved in the sodium fluoride solution. 1 ml aliquots of this solution are then dispensed through a 0.45 $\mu$ Millipore filter into 10 ml glass vials. The dispensed vials are placed in a freeze drier and when completely dry are sealed with PAC's under a nitrogen atmosphere. The sealed vials and their contents are then sterilised by exposure to 2.5 MRad of $\gamma$ irradiation.

(b) Labelling procedure

Using aseptic technique, 1-10 ml of sterile isotonic saline containing sodium pertechnetate-Tc-99m, conveniently obtained as the eluate from a sterile Technetium-99m generator, is injected through the PAC into a vial of the freeze-dried reagent. The vial, in a suitable radiation shield, is shaken for 10-15 seconds to ensure complete solution of the reagents and the preparation is then ready for intravenous injection of the calculated dose. The activity of Tc-99m added depends upon the number of patient doses to be taken from the vial but is usually in the range 2-50 mCi.

(c) Tissue distribution of the preparation in mice

Injection of 0.1 ml samples from 5 ml of Tc-99m labelled liver agent prepared as in example (b) into the tail veins of mice, followed by sacrifice 15 min. after injection gave the following information on dissected organ and tissue activity distribution:

|  | Percentage of total activity ($\pm$ S.D.) in each organ after kit storage periods of | | |
| --- | --- | --- | --- |
|  | 1-5 weeks (10 batches) (30 mice) | 11-15 weeks (3 batches) (9 mice) | 21-25 weeks (2 batches) (6 mice) |
| Liver and spleen | 92.9 $\pm$ 1.5 | 92.4 $\pm$ 0.5 | 90.0 $\pm$ 0.1 |
| Gut | 1.1 $\pm$ 0.5 | 1.2 $\pm$ 0.7 | 1.3 $\pm$ 0.4 |
| Lung | 1.5 $\pm$ 0.5 | 1.1 $\pm$ 0.6 | 3.8 $\pm$ 0.6 |
| Kidney | 0.5 $\pm$ 0.2 | 0.7 $\pm$ 0.3 | 0.5 $\pm$ 0.0 |
| Urine | 0.3 $\pm$ 0.2 | 0.6 $\pm$ 0.3 | 0.5 $\pm$ 0.3 |
| Blood | 0.2 $\pm$ 0.1 | 0.3 $\pm$ 0.2 | 0.2 $\pm$ 0.1 |
| Carcass | 3.6 $\pm$ 1.0 | 3.6 $\pm$1.2 | 3.6 $\pm$ 0.4 |

EXAMPLE 2

In a clinical assessment of the agent based upon our preferred formulation in Example 1 (a) and (b), over 300 patient investigations were carried out in four hospitals over a period of two months. The shelf-life of the packaged reagent was shown to be greater than twenty weeks and the labelled colloid was shown to be stable for at least seven hours after addition of Tc-99m pertechnetate to the freeze-dried reagent. The clinicians involved expressed the view that the scan quality observed was at least as good as that obtained with Tc-99m sulphur colloid agents described, in terms of diagnostic value.

What we claim is:

1. A packaged reagent for making Technetium-99m labelled tin colloids comprising:
   stannous tin, from 0.75 to 750 micrograms
   sodium potassium or ammonium ion, from 50 to 7000 micrograms,
   fluoride, from 40 to 5000 micrograms,
   and a container aseptically enclosing said reagent.

2. A packaged reagent as claimed in claim 1, wherein the reagent is a lyophilisate.

3. A packaged reagent as claimed in claim 1, wherein the reagent comprises 1 to 1000 micrograms of stannous fluoride and 0.1 to 10 milligrams of sodium, potassium or ammonium fluoride.

4. A packaged reagent as claimed in claim 3, wherein the reagent comprises about 125 micrograms of stannous fluoride and about 1 milligram of sodium fluoride.

5. A method of making a Technetium-99m labelled tin colloid, which method comprises adding Technetium-99m, as an aqueous solution of pertechnetate ion $TcO_4^-$, to a reagent comprising one part by weight of sodium, potassium or ammonium fluoride and from 0.00075 to 0.75 parts by weight of stannous tin.

6. A method as claimed in claim 5, wherein the Technetium-99m is used in the form of a solution of pertechnetate ion $TcO_4^-$ in isotonic saline.

7. A method as claimed in claim 5, wherein the reagent is the packaged reagent comprising
   stannous tin, from 0.75 to 750 micrograms
   sodium potassium or ammonium ion, from 50 to 7000 micrograms,
   fluoride, from 40 to 5000 micrograms, and
   a container aseptically enclosing said reagent.

8. A method as claimed in claim 5. wherein the solution of pertechnetate and the reagent are both sterile.

9. A method as claimed in claim 5. wherein from 2 to 50 mCi of Technetium-99m is used per mg of sodium, potassium or ammonium fluoride in the reagent.

10. A Technetium-99m labelled tin colloid when made by the method claimed in claim 5.

11. A method of visualising the liver of a mammal which comprises injecting into the mammal an amount of the Technetium-99m labelled tin colloid claimed in claim 10 to contain from 1 to 15 mCi of Technetium-99m, allowing the Technetium-99m to become located in the liver, and observing the gamma-radiation emitted by the liver.

* * * * *